(12) United States Patent
Miller

(10) Patent No.: US 10,406,315 B2
(45) Date of Patent: Sep. 10, 2019

(54) RELATION TO VALVES

(71) Applicant: INTERSURGICAL AG, Vaduz (LI)

(72) Inventor: Andrew Neil Miller, Wokingham (GB)

(73) Assignee: Intersurgical AG, Vaduz (LI)

( * ) Notice: Subject to any disclaimer, the term of this patent is extended or adjusted under 35 U.S.C. 154(b) by 0 days.

(21) Appl. No.: 14/758,889

(22) PCT Filed: Jan. 3, 2014

(86) PCT No.: PCT/EP2014/050062
§ 371 (c)(1),
(2) Date: Jul. 1, 2015

(87) PCT Pub. No.: WO2014/106648
PCT Pub. Date: Jul. 10, 2014

(65) Prior Publication Data
US 2015/0335852 A1    Nov. 26, 2015

(30) Foreign Application Priority Data

Jan. 3, 2013  (GB) .................................. 1300068.2

(51) Int. Cl.
*F16L 37/32*    (2006.01)
*A61M 16/20*    (2006.01)
(Continued)

(52) U.S. Cl.
CPC ...... *A61M 16/208* (2013.01); *A61M 16/0808* (2013.01); *F16K 3/029* (2013.01);
(Continued)

(58) Field of Classification Search
CPC .................................. F16L 37/30; F16L 37/32
(Continued)

(56) References Cited

U.S. PATENT DOCUMENTS 3,544,066 A * 12/1970 Fawkes ................. F16K 1/2263
251/306
4,942,901 A    7/1990 Vescovini
(Continued)

FOREIGN PATENT DOCUMENTS

| EP | 0795342 A2 | 9/1997 |
| EP | 2008684 A2 | 12/2008 |
| JP | 2002-130555 | 5/2002 |

OTHER PUBLICATIONS

Translation of JP 2002130555 A; Hishikawa Sukebumi; May 9, 2002.*

(Continued)

*Primary Examiner* — Michael R Reid
*Assistant Examiner* — Paul J Gray
(74) *Attorney, Agent, or Firm* — Pepper Hamilton LLP

(57) ABSTRACT

There is provided an apparatus for controlling fluid flow, comprising a first component for holding or conveying fluid, the first component having a port for the passage of fluid, a fluid passageway (18) from the interior of the first component to the exterior of the first component through the port, a contact valve (1) located in the fluid passageway (18), a second component having an abutment means, and connecting means for connecting the second component to the first component, the contact valve (1) comprising a first valve arm (8) extending into the fluid passageway (18), the first valve arm (8) being movable between an open position in which fluid flow through the fluid passageway (18) is substantially permitted, and a closed position in which fluid flow through the fluid passageway (18) is substantially prevented, wherein, when the second component is connected to the first component, the abutment means moves the first valve arm (8) into the open position.

9 Claims, 7 Drawing Sheets

(51) Int. Cl.
*F16K 3/04* (2006.01)
*F16K 3/02* (2006.01)
*F16K 21/04* (2006.01)
*A61M 16/08* (2006.01)
*F16L 37/30* (2006.01)
*A61M 39/26* (2006.01)
*A61M 39/24* (2006.01)
*A61J 1/10* (2006.01)
*A61J 1/20* (2006.01)

(52) U.S. Cl.
CPC ............... *F16K 3/04* (2013.01); *F16K 21/04* (2013.01); *A61J 1/10* (2013.01); *A61J 1/2037* (2015.05); *A61M 39/26* (2013.01); *A61M 2039/2433* (2013.01); *F16L 37/30* (2013.01); *F16L 37/32* (2013.01)

(58) Field of Classification Search
USPC .................. 137/614, 614.02, 614.03, 614.04
See application file for complete search history.

(56) References Cited

U.S. PATENT DOCUMENTS

| | | |
|---|---|---|
| 5,269,771 A | 12/1993 | Thomas et al. |
| 7,658,205 B1 | 2/2010 | Edelman et al. |
| 2003/0141477 A1 | 7/2003 | Miller |
| 2005/0015075 A1 | 1/2005 | Wright et al. |
| 2005/0187524 A1 | 8/2005 | Willis et al. |
| 2008/0185056 A1 | 8/2008 | Diodati et al. |
| 2009/0281526 A1 | 11/2009 | Kenny et al. |
| 2010/0253070 A1 | 10/2010 | Cheon et al. |
| 2010/0331787 A1 | 12/2010 | Fournie |
| 2011/0240158 A1* | 10/2011 | Py .................... A61M 39/18 137/614 |

OTHER PUBLICATIONS

International Preliminary Report on Patentability, Written Opinion of the International Search Authority, corresponding to PCT/EP2014/050062 dated Jul. 7, 2015.

International Search Report and Written Opinion corresponding to PCT/EP2014/050062 dated Jul. 16, 2014.

Great Britain Search Report corresponding to GB1300068.2 dated Apr. 9, 2013.

Examination Report for corresponding GB Application No. GB1804282.0, dated Jun. 18, 2018.

\* cited by examiner

SECTION C-C ved from the apparatus. In some embodiments of the invention, for example, a fluid collecting bag may be connected to a drainage port of a dehumidifier that removes moisture from respiratory gases, and collects moisture in the bag.

The first valve arm may be rotatable or pivotable between the open and closed positions. The first valve arm may be provided on a mounting wall of the valve, and may extend inwardly therefrom. These features are particularly advantageous because they each enable the valve member to be positioned in close proximity to the connection with the second component, and hence reduce loss of fluid during disconnection relative to the prior art. In addition, these features each enable the valve member to be formed integrally with the mounting wall, such that the valve member is deformable between open and closed positions, as discussed in more detail below, thereby reducing manufacturing costs.

The mounting wall may be circular in cross-section. The mounting wall may be a mounting tube and may be generally cylindrical. The first valve arm may extend generally radially inwardly relative to the mounting wall. The mounting wall may be adapted for connection to both male and female connectors.

The valve may comprise a second movable valve arm. The second valve arm may be movable, e.g. rotatable or pivotable, between an open position in which fluid flow through the valve is substantially permitted, and a closed position in which fluid flow through the valve is substantially prevented. The second valve arm may be arranged in opposition to the first valve arm. The first and/or second valve arm may extend in a direction which is generally perpendicular to the direction in which the fluid passageway extends.

The first and/or second valve arm may have an engagement surface adapted such that, in use, the engagement surface may be abutted by the abutment means in order to move the first and/or second valve arm from the closed position to the open position. The engagement surface may be offset or raised, in the direction in which the fluid passageway extends, from the remainder of the valve arm. The engagement surface may be raised relative to the surrounding surfaces of the valve, e.g. in the direction of engagement with the abutment means of the second component. The engagement surface may be provided on an engagement projection. The engagement projection may be defined on an exposed surface of the first and/or second valve arm. The engagement projection may project from a connection end of the port, and may be depressed relative to the connection end of the port in the open position of the first valve arm. The engagement projection may be depressed into a position in which the engagement surface is substantially flush with the global form of the connection end of the port, in the open position of the first valve arm. The engagement surface may be orientated substantially perpendicularly relative to the direction in which the fluid passageway extends.

The first and/or second valve arm may be adapted to deform, for example pivot, from the closed position to the open position. The first and/or second valve arm may be adapted to deform axially into the open position. The deformation may be resilient deformation. The first and/or second valve arm may be formed integrally with the mounting wall, which may enable a valve of unitary construction to be provided. The valve of unitary construction may comprise at least a mounting wall, which defines at least part of the fluid passageway of the first component, and the one or more valve arms.

RELATION TO VALVES

This application is a national stage application under 35 U.S.C. § 371 of PCT Patent Application Serial No. PCT/EP2014/050062, filed Jan. 3, 2014, which claims the priority benefit of Great Britain Application No. 1300068.2, filed Jan. 3, 2013.

This invention relates to valves for controlling the flow of fluids in a system, particularly in the field of medicine.

A common requirement in the field of medicine is the removal of fluid, and particularly liquid, from apparatus, for example for disposal or testing. There is therefore a need for an arrangement in which a vessel drainage port of apparatus containing fluid can be reliably opened and fluid removed. The arrangement should allow the drainage port to be reliably closed again, once the fluid has been removed. This is particularly important in the field of medicine as the fluid involved may have been taken from a patient with an infectious condition, and so may cause infection in a clinician coming into contact with the fluids.

Conventional apparatus relies on the use of deformable drainage tubes, and clamps for closing those tubes. For example, a flexible drainage bag may be connected to a drainage port of medical apparatus, and receive fluid through the drainage tube. Typically, a clamp is applied to the end of the drainage tube connected to the drainage bag, and the drainage bag is then removed. A replacement bag is then connected to the drainage tube, and the clamp is removed. However, this method of disconnecting the drainage bag has numerous disadvantages including the need for a flexible drainage tube, the need for a separate component, such as a clamp, to be used to close the drainage tube, and the risk of some liquid, at least, being exposed to the surroundings.

It is known in non-medical fields to use a Schrader valve to control fluid flow; this type of valve comprising an axially extending valve stem, which is spring-loaded into a closed position. However, these types of valves are expensive, due to the number of different parts, and may result in significant loss of fluid due to the dead space created by the valve stem.

There has been devised a valve and apparatus for controlling fluid flow which overcome or substantially mitigate some or more of the above mentioned and/or other disadvantages associated with the prior art.

According to a first aspect of the invention, there is provided an apparatus for controlling fluid flow, comprising a first component for holding or conveying fluid, the first component having a port for the passage of fluid, a fluid passageway from the interior of the first component to the exterior of the first component through the port, a second component having an abutment means, and connecting means for connecting the second component to the first component, the fluid passageway including a first valve comprising a first valve arm extending into the fluid passageway, the first valve arm being movable between an open position in which fluid flow through the fluid passageway is substantially permitted, and a closed position in which fluid flow through the fluid passageway is substantially prevented, wherein, when the second component is connected to the first component, the abutment means moves the first valve arm into the open position.

The apparatus according to the invention is advantageous principally because it enables an arrangement in which a first component containing fluid can be reliably drained into a second component, when the second component is connected to a port in the first component. The present application is particularly advantageous in relation to medical The first and/or second valve arm may be provided with a first and/or second valve surface for engaging a valve seat. In the closed position, the first and/or second valve surface may engage the valve seat, preventing fluid flow through the valve. In the open position, the first and/or second valve surface may separate from the valve seat, permitting fluid flow through the valve. The first and/or second valve surface may be adapted to form a fluid-tight seal with the valve seat. The first and/or second valve surface may be generally planar and may lie in an axial plane of the fluid passageway. The first and/or second valve surface may be arranged at an end of the first and/or second valve arm remote from the mounting wall. In embodiments having both first and second valve arms, the valve seat that may be engaged by the first valve surface may be the second valve arm, and the valve seat that may be engaged by the second valve surface may be the first valve arm. In preferred embodiments, the valve surface is provided on a spacing portion of the first and/or second valve arm such that the valve surface is spaced along a principal axis of the fluid passageway from the location on the enclosing wall from which the first and/or second valve arm extends. The first and/or second valve arm may have a first and/or second support portion extending in a direction generally orthogonal to the direction in which the fluid passageway extends.

The valve surface may be separated from the engagement surface of the valve arm, particularly where the valve arm is movable about a pivot, such that a fluid passageway is defined in the opening position between the engagement surface and the valve surface of the valve arm.

The valve may be provided with a biasing means for urging the first and/or second valve arm into the closed position. In preferred embodiments, the first and/or second valve arm may be deformable between the open position and the closed position. The material from which the first and/or second valve arm is formed may be deformable and is preferably resiliently deformable. In these embodiments, the biasing means is provided by the resilience of the valve arm. The first and/or second valve arm may be integral with the mounting wall and may be formed from the same material as the mounting wall. In use, if the abutment means is disengaged from the engagement surface, the biasing means may cause the first and/or second valve arm to return to the closed position.

The first component may be for collecting fluid. The first component may be connectable to a respiratory circuit. The first component may be adapted to collect fluid from the respiratory circuit, e.g. as part of a dehumidifier. The fluid may be liquid, and may comprise, or substantially consist of, water.

In other embodiments, the first component is for conveying fluid. The first component may be a tube. The valve may be adapted to receive an end of the tube and be retained thereon. The valve may be retained thereon by a friction fit. Alternatively, the valve may be adapted to be located within an end of the tube and retained therein. In these embodiments, the valve may be retained therein by a friction fit. The tube may be a drainage tube for respiratory fluids.

The valve may comprise a mounting wall and one or more valve members, at least. In presently preferred embodiments, the valve is connectable to the interior or exterior of a port, for example in the form of an opening or a tubular housing, for example by provision of interior and exterior formations adapted to engage the port. These formations may be formed on, or extend from, the mounting wall of the valve. This enables a single valve design to be utilised in a greater number of different applications.

In some embodiments, the valve is integral with the first component. The valve may be integrally formed with a wall of the first component.

In alternative embodiments, the valve is engageable with the first component. The valve may be connectable to the first component and may be releasably connectable to the first component. The port may be an opening in a wall of the first component. The valve may be adapted to be received in the port. The mounting wall of the valve may be adapted to be received in the port. The mounting wall may be retained in the opening by frictional engagement.

The valve may be provided with a gripping means for gripping the port. The gripping means may be provided on the mounting wall. The gripping means may be provided on an outer surface and/or on an inner surface of the mounting wall. The gripping means may be a projection. There may be a plurality of projections. The projections may be ridges. The ridges may extend in the plane in which the mounting wall extends. The ridges may extend over the circumference of the mounting tube. There may be three ridges.

The valve may be provided with a locating means. The locating means may be adapted to locate the valve in the opening. The locating means may be a locating projection on an outwardly facing surface of the mounting tube. In use, the valve may be located in an opening in a wall of the first component and the projection may be adapted to abut the wall. The locating projection may extend radially outwardly from the mounting tube. The locating projection may have an abutting surface, adapted to abut the rim of an opening in which the valve is located. The abutting surface may extend in the plane in which the mounting tube extends. The locating projection may be a flange, and may extend the full circumference of the mounting tube.

The second component may comprise a fluid conduit and may have a fluid flow path. The apparatus may be adapted such that the fluid passageway of the first component is in fluid communication with the fluid flow path of the second component when the second component is connected to the first component. Preferably, the fluid passageway is sealingly connected to the fluid flow path when the second component is connected to the first component.

A fluid control means may be provided in the fluid flow path. The fluid control means may be provided in an opening in the second component. The opening may be a fluid entry port. The fluid control means may be a valve. Preferably, the abutment means is operably linked to the fluid control means. Preferably, when the abutment means abuts the engagement surface of the first valve arm, the reaction force provided by the engagement surface moves the abutment means, causing the fluid control means to allow fluid to pass. The fluid control means may be a valve. The valve may have some or all of the features of the valve defined above.

The first and/or second valve may be provided in a first and/or second component. Where the apparatus comprises two valves, with respective abutment surfaces adapted for engagement with respective valve arms, the apparatus is particularly advantageous because the space between the valve surfaces of the respective valves may be reduced relative to the prior art, thereby reducing the amount of fluid external of the valves following disconnection.

In particular, the first component may include abutment means, and the second component may comprise a port for the passage of fluid, and a fluid passageway from the interior of the second component to the exterior of the second component through the port, the fluid passageway of the second component including a valve comprising a first valve arm extending into the fluid passageway, the first valve arm being movable between an open position in which fluid flow through the fluid passageway is substantially permitted, and a closed position in which fluid flow through the fluid passageway is substantially prevented, wherein, when the second component is connected to the first component, the abutment means of the first component moves the first valve arm into the open position.

The engagement surface of the first and/or second valve arm of the first component may be the abutment means of the first component. Similarly, the engagement surface of the first and/or second valve arm of the second component may be the abutment means of the second component.

It is believed the valve is new and has applications in many different fields, hence according to a further aspect of the invention there is provided a valve comprising a mounting wall defining a fluid passageway, the mounting wall being provided with a first valve arm extending inwardly into the passageway, the first valve arm being movable between an open position in which fluid flow through the valve is substantially permitted, and a closed position in which fluid flow through the valve is substantially prevented. The first valve arm may be provided with an engagement surface adapted to be engaged by a solid element to move the first valve arm, the engagement surface being offset from the remainder of the first valve arm in the direction in which the fluid passageway extends. The first valve arm may be rotatable or pivotable between the open and closed positions.

The invention according to this aspect of the invention is particularly advantageous because it enables the valve member to seal the fluid passageway in close proximity to the end of the fluid passageway of the valve at which the valve member is engaged during operation, and hence reduce loss of fluid during disconnection relative to the prior art. In addition, the present invention enables the valve member to be formed integrally with the mounting wall, such that the valve member is deformable between open and closed positions, as discussed in more detail above, thereby reducing manufacturing costs.

This valve may have some or all of the features defined above in relation to the valve provided in the apparatus according to the invention.

A preferred embodiment of the invention will now be described in detail, by way of illustration only, with reference to the accompanying drawings, in which FIG. 1 is a perspective view from above of a valve in accordance with the invention;

Figure 1:
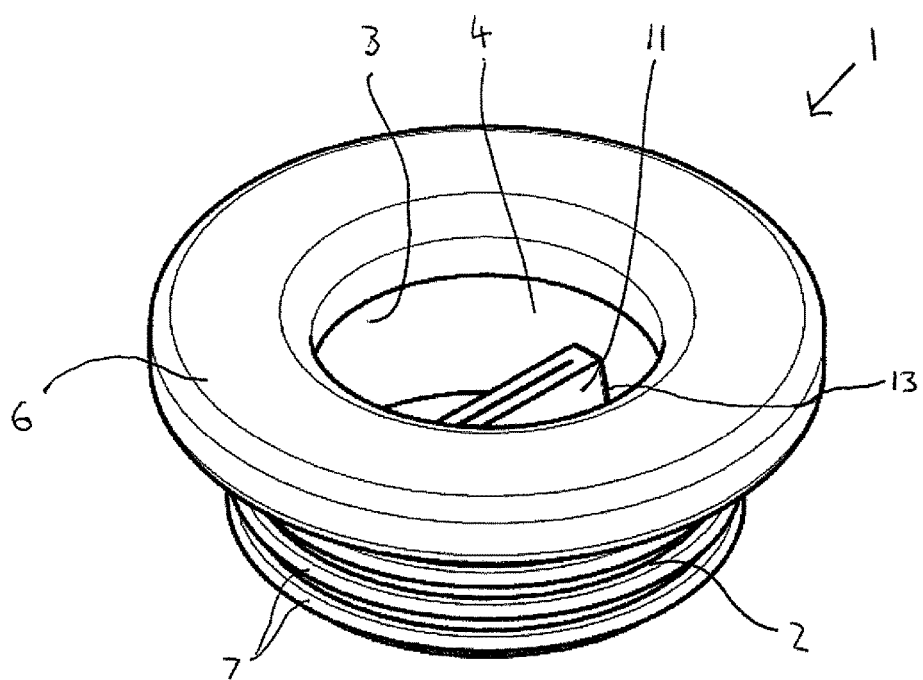
Figure 2:
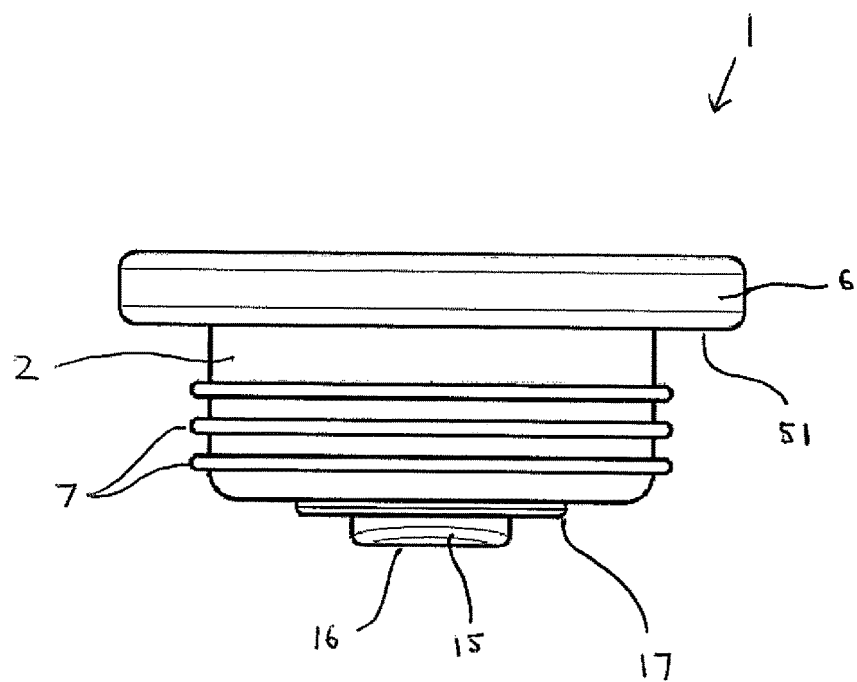
FIG. 2 is a side view of a valve in accordance with the invention.
Figure 3:
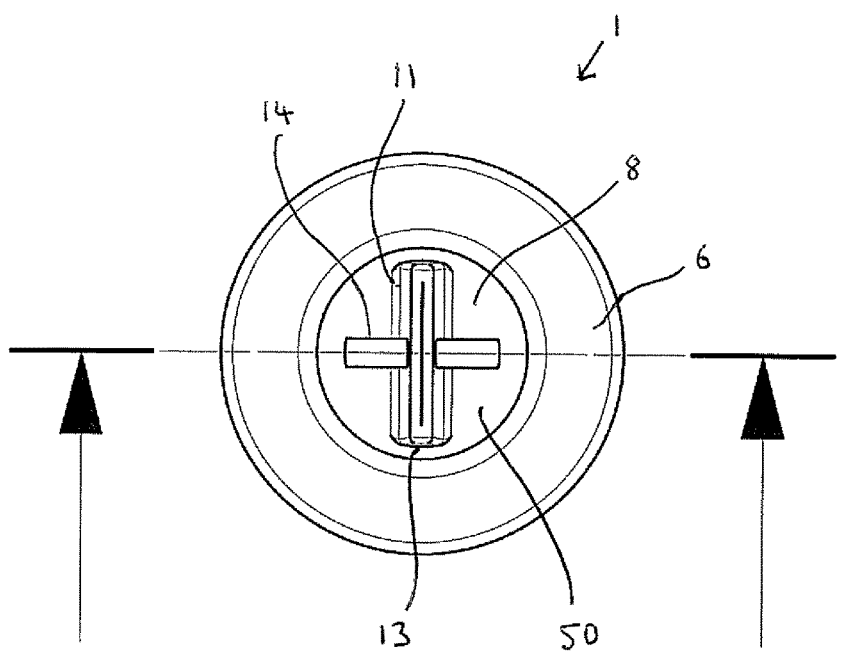
FIG. 3 is a plan view of a valve in accordance with the invention.
Figure 4:
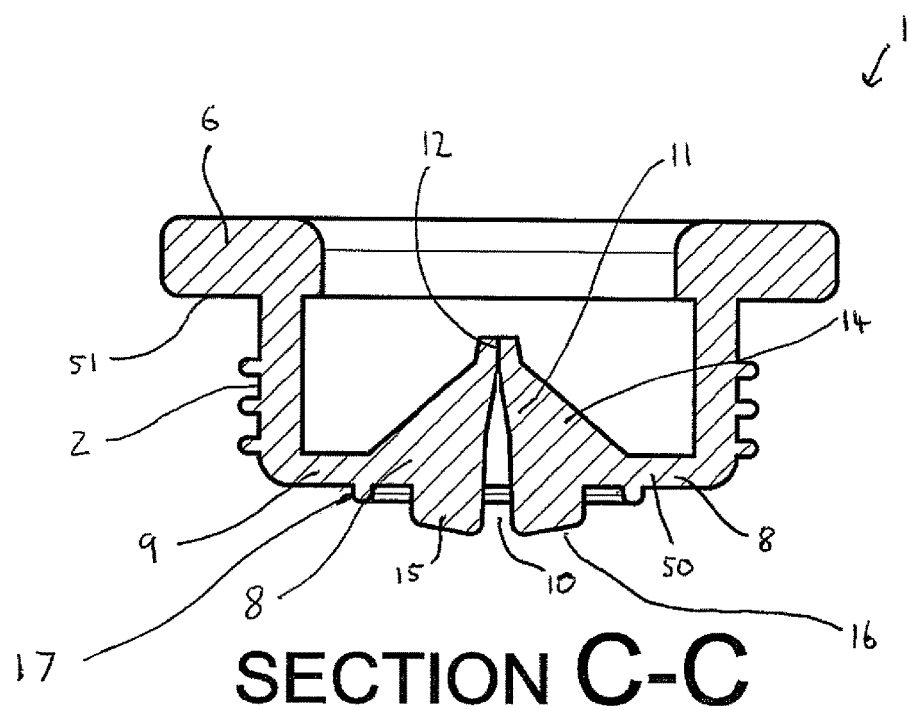
FIG. 4 is a cross-sectional front view of a valve in accordance with the invention, along the line C-C of FIG. 3.
Figure 5:
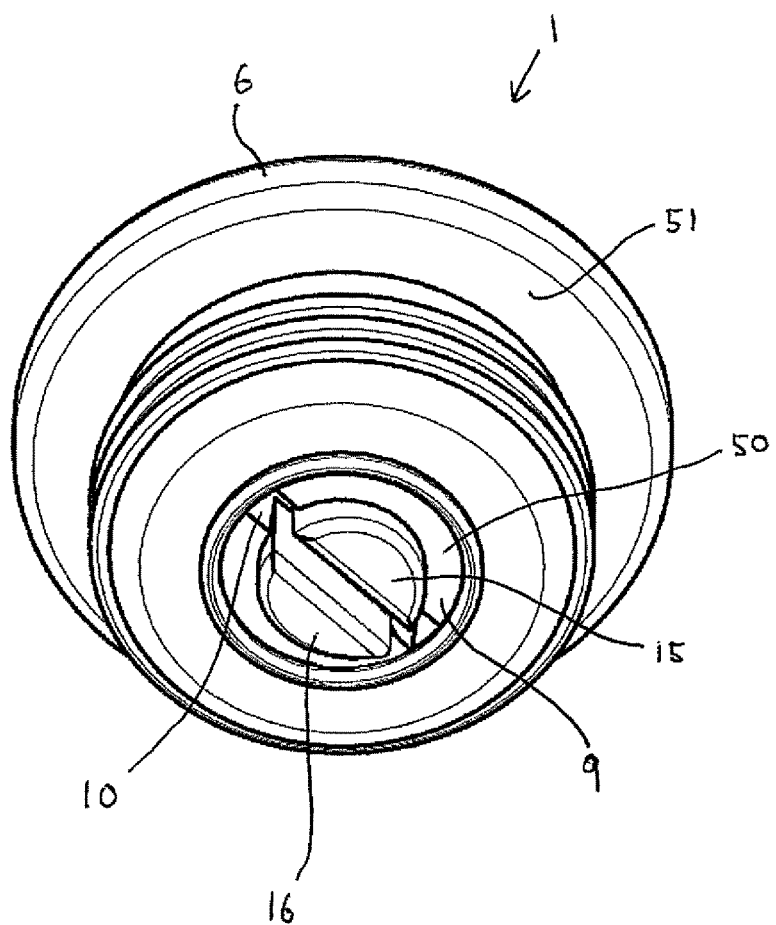
FIG. 5 is a perspective view from below of a valve in accordance with the invention.
Figure 6:
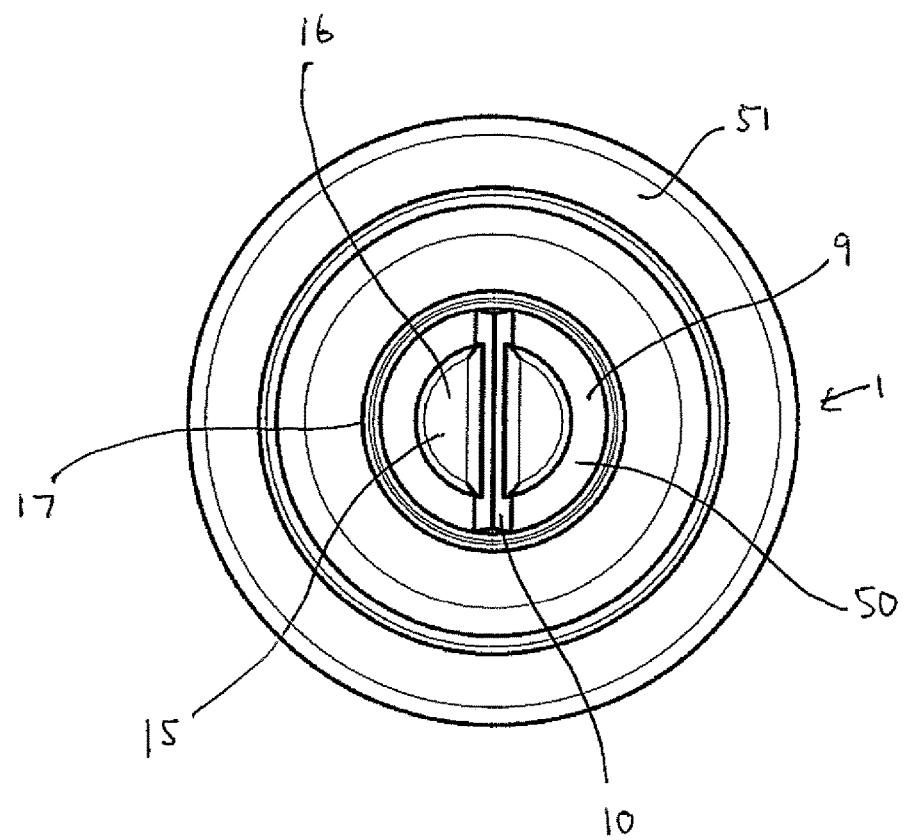
FIG. 6 is an underside view of a valve in accordance with the invention.

The contact valve 1 comprises a short, generally cylindrical mounting tube 2. The mounting tube 2 comprises a side wall 3 with a central, axially extending bore 4 of circular cross-section constituting a fluid passageway. The mounting tube 2 is provided with a locating flange 6 at one end. The locating flange 6 extends both radially outwardly and, to a lesser extent, radially inwardly. The free edges of the locating flange 6 are provided with a rounded chamfer. An abutment surface 51 is provided on the underside of the locating flange 6.

The outwardly facing surface of the mounting tube 2 is provided with three lateral ridges 7 which are axially spaced along the mounting tube 2 and extend along the full circumference of the mounting tube 2. The ridges 7 form a grip structure, such that, if the mounting tube 2 is inserted in an appropriately-sized cylindrical bore, the ridges 7 are able to grip the interior wall of the bore 4.

A pair of opposing valve members 8 are provided at the end of the mounting tube 2 remote from the flange 6. The valve members 8 each comprise a support portion 50 and a lip portion 11. The support portion 50 is defined by a flexible, resilient, circular diaphragm 9 extending radially inwardly from the walls of the mounting tube 2. A generally rectangular slit 10 is provided in the diaphragm 9, which extends part of the way across the diaphragm 9, along a diameter thereof.

The lip portions 11 are generally rectangular, planar members, upstanding from the support portion. The lip portions 11 extend along the edge of the slit 10 and extend a short distance beyond each end of the slit 10. The lip portion 11 extends generally upwardly, but is slightly inclined towards the central axis of the slit 10.

A valve surface 12 is provided in an upper region of each lip portion 11. The valve surface 12 is elongate and rectangular in shape, extending along the width of the lip portion 11. The valve surface 12 lies in an axial plane. When the valve 1 is in the closed configuration, each valve surface 12 is adapted to lie flat against the other such that the two valve surfaces 12 are in sealing engagement.

The lip portions 11 are provided with opposing end sections 13 for connecting the side edges of the lip portions 11 together. The end sections 13 are upstanding from the circular diaphragm 9. Each end section 3 is generally prism-shaped and its edges have a rounded chamfer.

Each valve member 8 is provided with a stiffener 14. Each stiffener 14 is generally wedge-shaped, i.e. of generally triangular cross-section. Each stiffener 14 is upstanding from an upper surface of the circular diaphragm 9 and abuts a lip portion 11. The stiffener 14 urges the lip portion 11 into the closed configuration.

Each valve member 8 is provided with an abutment portion 15 which depends downwardly from the underside of the circular diaphragm 9. The abutment portion 15 has the general form of a half cylinder, the straight edge lying along the edge of the slit 10. The straight edge of the abutment portion 15 is shorter than the slit 10.

The edges of the abutment portion 15 have a rounded chamfer. The downwardly-facing surface of the abutment portion 15 constitutes an abutment surface 16. The abutment surface 16 is inclined relative to the circular diaphragm 9 such that the thickest part of the abutment portion 15 is closest to the slit 10.

A seal 17 is provided on the underside of the circular diaphragm 9. The seal 17 constitutes a downwardly depending annular lip. The seal 17 surrounds the slit 10 and is concentric with the mounting tube 2.

The contact valve 1 is formed as a unitary piece of silicone rubber or another thermoplastic elastomer by single-shot injection moulding.

Figure 7:
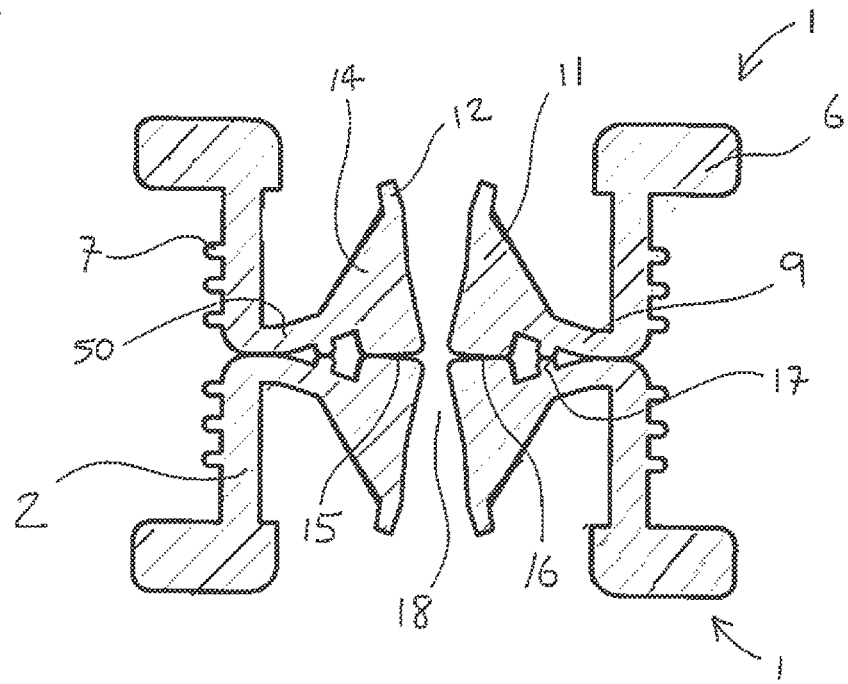
FIG. 7 is a cross-sectional view from the side of two valves in use in accordance with the invention.

Applying an upward force to the abutment portions 15 causes the valve members 8 and, in particular, the support portions 50, to deform such that the lip portions 11 deflect upwardly. This causes the valve surfaces 12 to separate, causing a fluid passageway 18 between the valve surfaces 12 to be created. This is seen best in FIG. 7. The separation of the valve surfaces 12 is greater in the mid portion of the valve surfaces 12, as the end sections 13 prevent substantial separation of the end regions of the valve surfaces 12. The fluid passageway 18 is therefore generally cylindrical in form.

When the upward force is removed, the resilience of the valve members 8 causes the valve members 12 to return to the rest configuration in which the valve surfaces 12 are in mutual engagement.

In preferred embodiments, the valve 1 is used in conjunction with a bag for collecting condensate from a respiratory circuit. Such bags can be connected to a drainage port of a dehumidifier for removing moisture from a respiratory circuit. The dehumidifier removes water from a respiratory circuit and the water passes through the drainage port into the bag. When the bag is full, bag is disconnected from the drainage port for disposal.

The bag has an entry port for receiving water from the dehumidifier. The entry port is an opening in the wall of the bag, with an annular connecting collar upstanding on the outer surface of the bag and surrounding the entry port.

Figure 8:
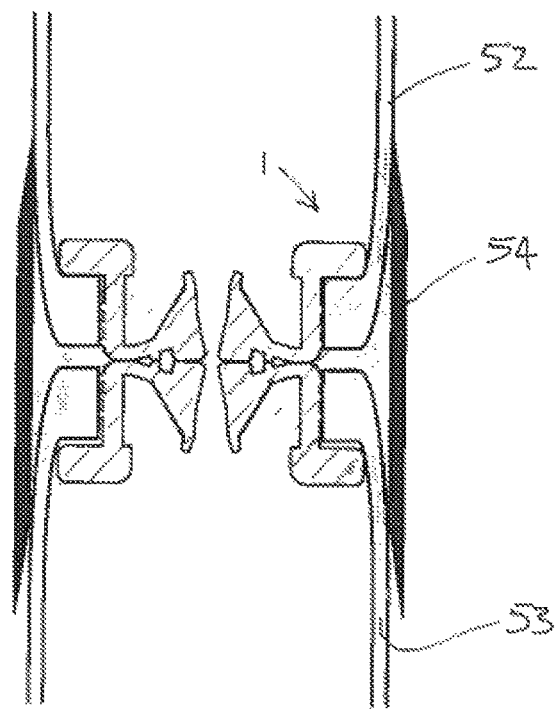
FIG. 8 is a cross-section view from the side of two valves in use in accordance with the invention illustrating a first component, a second component, and a connector.

As shown in FIG. 8, the drainage port of the dehumidifier comprises a cylindrical fluid conduit or first component 52 for conveying water removed from respiratory gases in a breathing circuit. The fluid conduit or first component 52 has proximal and distal ends, the ends being open. An annular connecting collar or connector 54 is provided at the distal end of the fluid conduit for connection to the connecting collar 54 of the collecting bag or second component 53.

The contact valve 1 according to the invention is adapted to be received in the opening defining the entry port of the collecting bag. In particular, the contact valve 1 is located in the opening such that the abutment portions 15 of the valve members 8 project outwardly from the bag. In particular, the mounting tube 2 of the valve 1 is received, with a friction fit, in the opening. The ridges 7 on the outer surface of the mounting tube 2 assist in providing the friction fit. Furthermore, the abutment surface 51 of the locating flange 6 abuts an interior surface of the bag. The contact valve 1 received in the entry port of the collecting bag will be referred to below as the "bag valve".

A further contact valve 1 according to the invention is adapted to be located in the distal end of the fluid conduit of the drainage port. In particular, the distal end of the fluid conduit is received within the mounting tube 2 and retained with a friction fit. The valve 1 is orientated such that the abutment portions 15 of the valve members 8 project outwardly from the distal end of the fluid conduit. The valve 1 located in the fluid conduit of the drainage port will be referred to below as the "drainage valve".

When the bag is not connected to a drainage port, no force is applied to the abutment portions 15 of the valve members 8 of the bag valve, such that the valve members 8 remain in a closed configuration and passage of fluid through the valve 1 is substantially prevented. Connecting the bag to the drainage tube causes the abutment surfaces 16 of the abutment portions 15 of the drainage valve to engage the abutment surfaces 16 of the abutment portions 15 of the bag valve. This applies an axial force to the abutment portions 15 of the bag valve, causing the valve members 8 to deflect axially. This opens a fluid passageway through the bag valve. Furthermore, the engagement of the abutment surfaces 16 applies a force, in the opposite direction, to the abutment portions 15 of the drainage valve, causing the valve members 8 of the drainage valve to deflect axially, thereby opening a fluid passageway through the drainage valve. A fluid passageway between the interior of the bag and the interior of the drainage port is thus opened, allowing fluid from the drainage port to pass into the bag.

In this configuration, the annular seals 17 provided on the bag valve and the drainage port abut one another. The abutment of the seals creates a fluid-tight barrier, such that the escape of fluid from the fluid passageway by passing between the seals 17 is substantially prevented.

When the bag is full, the bag is disconnected from the drainage port. This causes the respective abutment surfaces on the bag and drainage valves to separate, removing the opposing forces on the respective valve members. The resilience of the valve members causes them to return to the closed position, wherein the valve surfaces 12 lie flat against each other, creating a seal therebetween. Thus the fluid passageway through the valves is closed. Further passage of fluid out of the drainage port through the exit port is therefore substantially prevented, until a replacement bag is connected.

The invention claimed is:

1. An apparatus for controlling fluid flow, comprising:
a first component for holding or conveying fluid, the first component having a port for the passage of fluid, a fluid passageway from the interior of the first component to the exterior of the first component through the port, a second component having an abutment, and a connector for connecting the second component to the first component, the fluid passageway including a valve comprising a first valve arm and a second valve arm provided on opposing mounting walls of the valve and extending inwardly into the fluid passageway, the first valve arm having a first engagement surface and a first valve surface, the second valve arm having a second, engagement surface and a second valve surface, the first valve arm and the second valve arm being movable between an open position in which fluid flow through the fluid passageway is permitted, and a closed position with the first valve surface and the second valve surface contacting each other to provide a sealing engagement in which fluid flow through the fluid passageway is prevented, wherein the valve is adapted to be received in the port, and wherein, when the second component is connected to the first component, the first engagement surface and the second engagement surface are abutted by the abutment such that an initial contact between the first engagement surface and the second engagement surface and the abutment causes the first valve arm and the second valve arm to move from the closed position to the open position and wherein the first engagement surface is provided on a first engagement projection of the first valve arm, the second engagement surface is provided on a second engagement projection of the second valve arm, and the first valve arm and the second valve arm are flexible to pivot and resiliently deform between the closed position with the first valve surface and the second valve surface contacting each other and the open position, wherein the first component includes a further abutment, and the second component comprises a second port for the passage of fluid, and a second fluid passageway from the interior of the second component to the exterior of the second component through the second port, the second fluid passageway including a second valve comprising a further first valve arm extending into the fluid passageway, the further first valve arm being movable between an open position in which fluid flow through the second fluid passageway is permitted, and a closed position in which fluid flow through the second fluid passageway is prevented, wherein, when the second component is connected to the first component, the further abutment of the first component moves the further first valve arm into the open position.

2. The apparatus as claimed in claim 1, wherein the first and second engagement projections project toward a connection end of the port, and are depressed away from the connection end of the port in the open position of the first valve arm and the second valve arm.

3. The apparatus as claimed in claim 1, wherein the first and second engagement projections are depressed into a position in which the engagement projections are substantially flush with a connection end of the port, in the open position of the first valve arm and the second valve arm.

4. The apparatus as claimed in claim 1, wherein the valve is releasably connected to the first component.

5. The apparatus as claimed in claim 1, wherein the valve is provided with a gripping means for gripping the post.

6. The apparatus as claimed in claim 1, wherein the valve is provided with a locating flange.

7. The apparatus as claimed in claim 1, wherein the engagement surface of the first valve arm of the first component also provides the further abutment of the first component.

8. The apparatus as claimed in claim 1, wherein the further first valve arm of the second component has a further engagement surface adapted such that, in use, the further engagement surface is abutted by the further abutment of the first component in order to move the further first valve arm of the second component from the closed position to the open position, and the further engagement surface of the further first valve arm of the second component is also the abutment of the second component.

9. The valve as claimed in claim 1, wherein the mounting wall of the valve is adapted to be received in the port.

* * * * *